United States Patent [19]

Nakamura et al.

[11] Patent Number: 5,914,424
[45] Date of Patent: Jun. 22, 1999

[54] PROCESS FOR PRODUCING ACRYLONITRILE

[75] Inventors: Toshio Nakamura; Hachiro Arai; Hideyuki Inaba; Hiroshi Yamamoto, all of Yokohama, Japan

[73] Assignee: Mitsubishi Rayon Co., Ltd., Japan

[21] Appl. No.: 08/965,021

[22] Filed: Nov. 5, 1997

[30] Foreign Application Priority Data

Nov. 6, 1996 [JP] Japan ................................. 8-294122

[51] Int. Cl.$^6$ .................................................. C07C 253/24
[52] U.S. Cl. ........................................... 558/315; 558/435
[58] Field of Search ........................................ 558/315, 435

[56] References Cited

U.S. PATENT DOCUMENTS

| | | | |
|---|---|---|---|
| 4,102,914 | 7/1978 | Beuther et al. | 260/465.3 |
| 4,246,192 | 1/1981 | Pujado | 260/465.3 |
| 4,339,394 | 7/1982 | Grasselli et al. | 260/465.3 |
| 4,668,802 | 5/1987 | Contractor | 549/259 |

*Primary Examiner*—Johann Richter
*Assistant Examiner*—Ebenezer Sackey
*Attorney, Agent, or Firm*—Wenderoth, Lind & Ponack

[57] ABSTRACT

In a process for producing acrylonitrile by the ammoxidation of propylene, comprising bringing, in a fluidized-bed reactor, a gas containing propylene, ammonia and molecular oxygen into contact with a highly-active ammoxidation catalyst (this catalyst being one which can attain a rate constant of 2 s$^{-1}$ or more for the ammoxidation reaction of propylene, assuming that the reaction is a first-order reaction) which is in a state of being fluidized by the gas, the improvement comprising carrying out the ammoxidation under the following conditions:

(a) the superficial gas velocity in the fluidized-bed reactor is maintained at 1 to 10 m/s under such an operation condition that the rate constant of the ammoxidation reaction of propylene is 2 s$^{-1}$ or more, assuming that the reaction is a first-order reaction;

(b) an area in which the density of fluidized solid matter is 100 kg/m$^3$ or more is kept in the fluidized-bed reactor at the upstream side thereof; and (c) a system for recycling the ammoxidation catalyst which has been supplied to the reaction is provided in the fluidized-bed reactor between the upstream side and downstream side thereof, and the recycling catalyst is introduced into the reactor at such a position that the weight ratio of the ammoxidation catalyst present in an area above the introduction position to the ammoxidation catalyst present in an area below the position will be from 2:1 to 99:1.

5 Claims, 2 Drawing Sheets

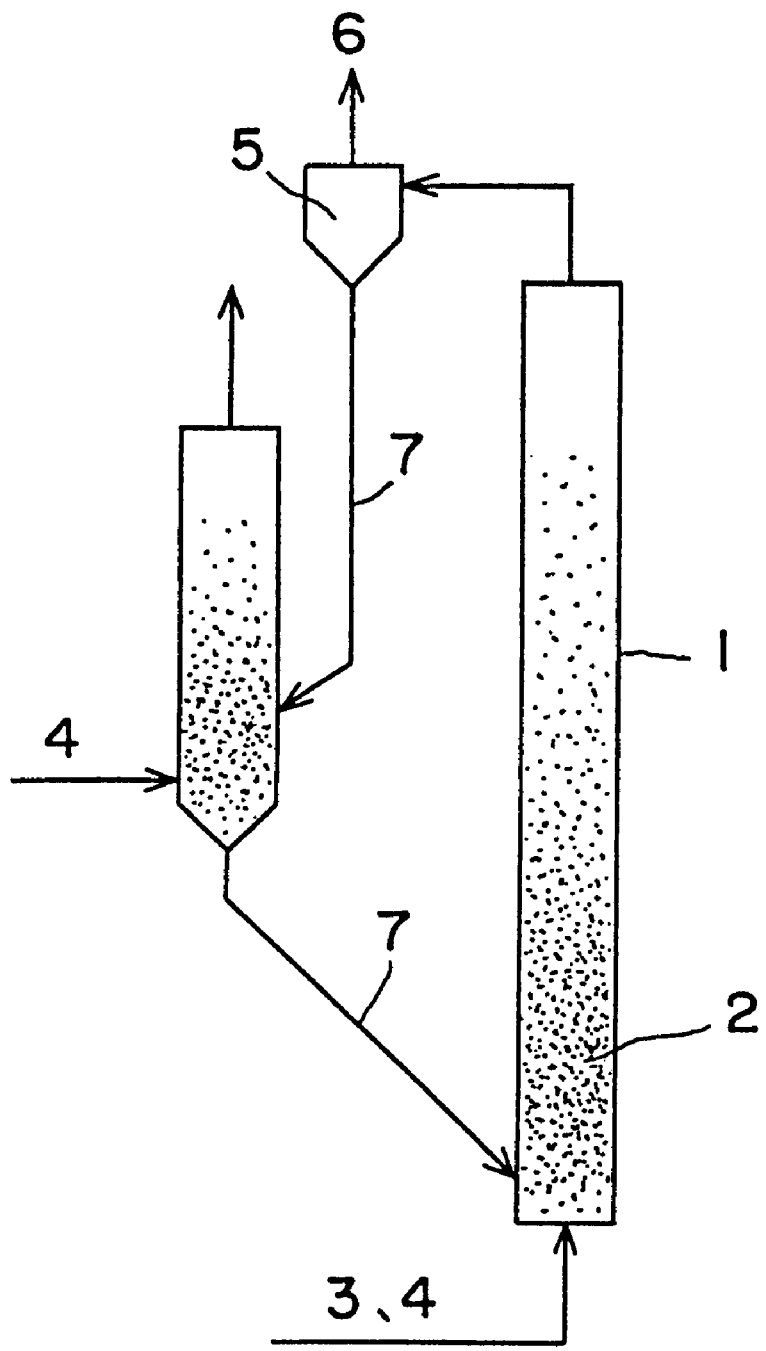
F I G. 3

PROCESS FOR PRODUCING ACRYLONITRILE

BACKGROUND OF THE INVENTION

1. Field of the Invention

This invention relates to an improved process for the production of acrylonitrile by the catalytic ammoxidation of propylene in a fluidized-bed reactor, which can produce acrylonitrile in a high yield at a low production cost.

2. Background Art

Reaction for synthesizing acrylonitrile by means of the ammoxidation of propylene is, in general, accompanied by high heat generation. For this reason, a method using a fluidized-bed reactor, which is advantageous to the removal of heat generated, is often employed. However, the conventional technique using such a method tends to have the following problems: the back mixing of a gas is unavoidable due to the violent mixing of particles which is caused in a fluidized bed; and the yield of acrylonitrile is lowered due to the progress of unfavorable side reaction which is caused when contact between a gas and a catalyst becomes insufficient because of bubbles formed in a fluidized-bed reaction area. In particular, when it is intended to attain high productivity by using a highly-active catalyst, not only the yield of acrylonitrile is remarkably lowered, but also it becomes difficult to remove heat of reaction. As a result, it becomes impossible to maintain the reaction temperature in a desirable range, and finally becomes impossible to continue the reaction. In addition, in the case of a highly-active catalyst, it is enough to use it in only a small amount, so that the volume of the catalyst bed is small. The optimum height of the catalyst bed is therefore short, so that it may be difficult to secure, in the catalyst bed, the heat transfer surface area on a cooling coil needed for the removal of heat of reaction and that the influence of back mixing may become great.

As solutions for the aforementioned problems, there have been known, for example, those methods which are proposed in Japanese Patent Publications No. 28491/1969, No. 531/1973 and No. 38428/1983, and U.S. Pat. No. 3,230,246 and No. 3,783,528. In these methods, obstacles such as shaped metallic articles, screens, grids, perforated plates, horizontal plates, pipes or the like are laid in a catalyst bed to prevent the coalescence or growth of bubbles, or to prevent the back mixing of a gas, thereby improving contact between the feed gas and the catalyst. However, as far as the present inventors know, these methods are not practical because construction for laying the obstacles is complicated; and, in addition, they seem to have the following problems: the mixing of catalyst particles is prevented by the obstacles, so that the favorable features of fluidized bed (e.g., excellent temperature controllability, and uniform catalyst bed temperature) are lost; and the distribution of the catalyst in the reactor becomes uneven in terms of space and time, so that it becomes difficult to stably and continuously conduct the operation.

In order to prevent the lowering of contact efficiency that is caused by the back mixing of a gas and by the formation of bubbles, Japanese Patent Laid-Open Publication No. 144528/1978 proposes a method for attaining high acrylonitrile yield by using a fluidized bed with a high gas velocity of approximately 1.5 to 7.5 m/sec. However, even this method seems to be unsatisfactory for economically attaining high productivity by the use of a highly-active catalyst. A particular problem in this method is that a considerably long reactor is required to attain a predetermined rate of reaction because the superficial gas velocity in a column is high. An increased cost is needed to construct such a reactor for use in an industrial-scale apparatus, and this becomes a great economical burden. To avoid this problem, it may be contemplated to make the reactor in the shape of a coil. In this case, however, another problem is brought about as follows: a gas and a catalyst are to flow in the coil with a circling movement, so that they are separated from each other due to centrifugal force, and the efficiency of contact between them is thus lowered. This problem is a fatal drawback in large-scale apparatuses for industrial use.

SUMMARY OF THE INVENTION

It is an object of the present invention to solve the above problems in the prior art and provide an economically advantageous process for producing acrylonitrile, which can make the best use of a highly-active catalyst in the vapor-phase catalytic ammoxidation of propylene using a fluidized-bed reactor and enables the high-yield, high-productivity production of acrylonitrile.

It has now been found by the present inventors that the efficiency of contact between a feed gas and a catalyst in the ammoxidation process is remarkably enhanced and thus the above object can be achieved when the ammoxidation is carried out under specific operational conditions.

Thus, the present invention provides in a process for producing acrylonitrile by the ammoxidation of propylene comprising bringing, in a fluidized-bed reactor, a gas containing propylene, ammonia and molecular oxygen into contact with a highly-active ammoxidation catalyst (this catalyst being one which can attain a rate constant of 2 s$^{-1}$ or more for the ammoxidation reaction of propylene, assuming that the ammoxidation reaction is a first-order reaction) which is in a state of being fluidized by the gas, the improvement comprising carrying out the ammoxidation under the following conditions:

(a) the superficial gas velocity in the fluidized-bed reactor is maintained at 1 to 10 m/s under such an operation condition that the rate constant of the ammoxidation reaction of propylene is 2 s$^{-1}$ or more, assuming that the reaction is a first-order reaction;

(b) an area in which the density of fluidized solid matter is 100 kg/m$^3$ or more Is kept in the fluidized-bed reactor at the upstream side thereof; and (c) a system for recycling the ammoxidation catalyst which has been supplied to the reaction is provided in the fluidized-bed reactor between the upstream side and downstream side thereof, and the recycling catalyst is introduced into the reactor at such a position that the weight ratio of the ammoxidation catalyst present in an area above the introduction position to the ammoxidation catalyst present in an area below the position will be from 2:1 to 99:1.

According to the present invention, acrylonitrile can be obtained in high yield and with high productivity from a gas containing propylene, ammonia and molecular oxygen by using a highly-active ammoxidation catalyst. Moreover, the construction cost of a reactor for use in the above process is low, so that acrylonitrile can be produced economically.

BRIEF DESCRIPTION OF THE DRAWINGS

In the drawings,

FIG. 3 is a schematic view of yet another apparatus usable for carrying out the process of the present invention.

DETAILED DESCRIPTION OF THE INVENTION

The preferred embodiment of the present invention will now be explained in detail by referring to the accompanying drawings.

Figure 1:
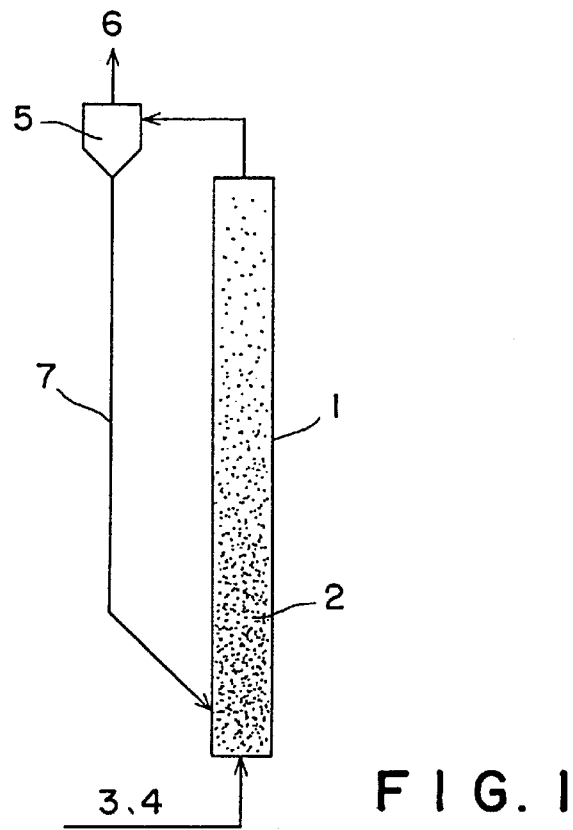
FIG. 1 is schematic view of an apparatus usable for carrying out the process of the present invention.
Figure 2:
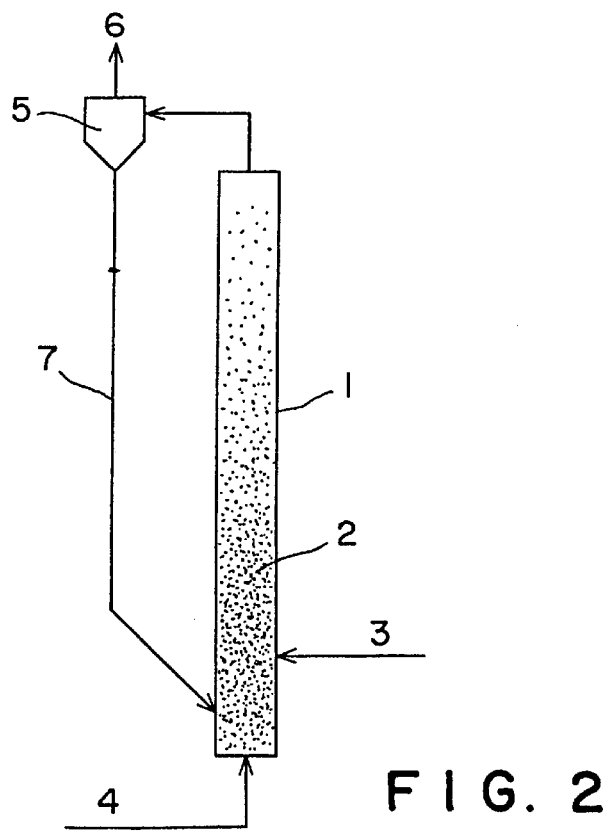
FIG. 2 is a schematic view of another apparatus usable for carrying out the process of the present invention.

To a fluidized-bed reactor 1 packed with fluidized solid matter comprising a highly-active ammoxidation catalyst, a feed gas containing propylene and ammonia or a feed gas containing propylene, ammonia and molecular oxygen is fed through a feed-gas feed line 3 (FIGS. 1 to 3). Besides the above three components, the feed gas can contain other purposive components or components which are inevitably present therein. It is thus possible to feed air as the molecular oxygen. In this case, the components of air other than oxygen, especially molecular nitrogen, are to co-exist in the feed gas. Moreover, it is also a common manner to add steam to the feed gas. In an embodiment shown in FIG. 2, molecular oxygen is fed to the fluidized-bed reactor 1 through a molecular oxygen-containing gas feed line 4.

The superficial gas velocity in the fluidized-bed reactor 1 is maintained at 1 to 10 m/s, preferably 1 to 9 m/s, more preferably 1 to 7 m/s under such a condition that, when the ammoxidation reaction of propylene is assumed to be a first-order reaction, the rate constant of the reaction is $2 \text{ s}^{-1}$ or more, preferably $3 \text{ s}^{-1}$ or more. When the superficial gas velocity is as high as 1 to 10 m/s as in the present invention, bubbles substantially disappear, and the degree of the back mixing of the gas becomes negligibly small. Contact between the gas and the catalyst is thus extremely excellent.

The rate constant of the reaction varies depending upon the activity of the catalyst used, the reaction temperature, the composition of a gas to be fed to a reactor, the superficial gas velocity in the reactor, the structure of the reactor, or the like. The rate constant of the reaction under given reaction conditions can be determined by the concentrations of propylene at the inlet and outlet of a reactor, and the contact time.

According to one characteristic feature of the present invention, an area in which the density of fluidized solid matter (comprising the highly-active ammoxidation catalyst 2, and other solids which may be used when necessary) is $100 \text{ kg/m}^3$ or more, preferably $150 \text{ kg/m}^3$ or more, more preferably $200 \text{ kg/m}^3$ or more is kept in the fluidized-bed reactor 1 at the upstream side thereof. When the density is less than $100 \text{ kg/m}^3$, the reaction at the upstream side of the fluidized-bed reactor cannot fully proceed, so that it is necessary to increase the height of the reactor. Such a low density is thus unfavorable.

In conventional processes of this type, in which acrylonitrile is produced under a fluidized state with a high gas velocity, the density of fluidized solid matter in a reactor is low. Therefore, the contact time required tends to be long even when a highly-active catalyst is used. In order to attain the required contact time, it is unavoidable to make the reactor remarkably long or extremely large in size. This results in an increase in construction cost, and is therefore economically disadvantageous. In order to solve this problem, in the present invention, the progress of the reaction is accelerated while keeping, in the fluidized-bed reactor 1 at the upstream side thereof, an area in which the density of fluidized solid matter is $100 \text{ kg/m}^3$ or higher.

The fluidized-bed reactor is generally upright. Therefore, the upstream side of the fluidized-bed reactor means the lower part of the reactor. Further, the position in the reactor at which the high-density area should be kept is, in general, lower than ½ of the height of the reactor (the height of the reactor means the distance between a gas feed opening positioned at the lowest part of the reactor at the upstream side thereof, and a gas discharge opening positioned at the topmost part of the reactor at the downstream side thereof).

The density of fluidized solid matter can be adjusted to a predetermined value by suitably selecting the superficial gas velocity in a reactor, the amount of a catalyst to be packed in the reactor, the particle diameter of the catalyst, the density of the catalyst particles, the position at which the recycling catalyst is returned to the reactor, and the position at which the gas containing propylene, ammonia and molecular oxygen is fed to the reactor. It is noted that the density of fluidized solid matter can be obtained by determining the difference between pressures measured at two different points along the height of the fluidized-bed reactor, and dividing it by the distance between the two points.

By being accompanied by the gas stream, the fluidized solid matter is conveyed to the upper part of the reactor 1, and separated from the gas stream by a catalyst separator 5 placed in the vicinity of the top of the reactor 1, or at the outside of the reactor 1. As the catalyst separator 5, a cyclone is usually used. If necessary, a multicyclone can be used (not shown in the figures).

The gas from which the highly-active ammoxidation catalyst (and other fluidized solids) has been separated, that is, a reaction product-containing gas is drawn out from the system, and transferred to a purification system 6. From this gas transferred, acrylonitrile, the desired product, is recovered by a conventionally known means.

On the other hand, the catalyst 2 collected by the catalyst separator 5 is introduced, as it is (FIGS. 1 and 2), or after subjected to a reactivation treatment (FIG. 3), into the fluidized-bed reactor 1 either continuously or intermittently through a catalyst-recycling line 7. In order to continue the reaction with maintaining, at a high level, the activity of the ammoxidation catalyst to be supplied to the reaction, it is preferable to return the catalyst to the reactor after subjecting it to an activation treatment (FIG. 3).

The catalyst-recycling system is, in general, formed in the fluidized-bed reactor between the downstream side and upstream side thereof. The term "downstream side" as used herein includes not only a reactor in a narrow sense which contains a fluidized catalyst bed to provide a place for reaction, but also, in the case where a reaction gas drawn out from this reactor still reacts because it contains the fluidized catalyst, a region outside the reactor in which such a reaction is proceeding, that is, the outside region including the cyclone in the case of the embodiment shown in FIG. 1.

The catalytic activity of the catalyst used has generally been lowered due to the deposition of coke and/or reduction (since the catalyst is generally composed of an oxide, it is usually reduced in the process of ammoxidation). Therefore, the catalyst is usually activated by heating it in an oxidizing atmosphere.

This heating can be conducted by any purposive method. It is however preferable to employ a fluidized bed in order to continuously activate and recycle the catalyst, and to uniformly heat the catalyst (FIG. 3). Thus, it is preferable to reactivate the ammoxidation catalyst which has passed through the catalyst separator 5 with a molecular oxygen-containing gas while fluidizing the catalyst by the gas. Any type of fluidized bed such as a conventional fluidized bed or a high-velocity fluidized bed may be used for this purpose.

As mentioned above, the reactivation treatment is usually carried out by bringing a catalyst to be treated into contact with a molecular oxygen-containing gas at a high temperature. As the molecular oxygen, air, oxygen-rich air, air diluted with steam, nitrogen or carbon dioxide, or the like can be used. Further, it is also possible to reactivate the catalyst by bringing it into contact with molecular oxygen and some of the active components of the catalyst. The reactivation treatment temperature varies depending upon the catalyst to be treated. It is however generally from 450 to 700° C., preferably from 480 to 600° C. The reactivation treatment time is generally from approximately 1 to 300 minutes, preferably from 10 to 120 minutes.

The catalyst drawn out of from the fluidized-bed reactor 1 is reintroduced into the reactor at such a position that the weight ratio of the ammoxidation catalyst present in an area above the position to the ammoxidation catalyst present in an area below the position will be from 2:1 to 99:1, preferably from 5:1 to 99:1, more preferably from 9:1 to 99:1.

The feed gas to be fed to the fluidized-bed reactor 1, that is, the gas containing propylene, ammonia and molecular oxygen is, in general, fed to the bottom of the reactor so that the fluidized bed which provides a place for reaction can be effectively utilized. However, a part of or the whole quantity of propylene or ammonia, and a part of a molecular oxygen-containing gas can also be fed from a position higher than the bottom of the reactor.

Further, as mentioned previously, the feed gas can be fed to the fluidized-bed reactor 1 after mixed with an inert gas such as steam, nitrogen or carbon dioxide; or the feed gas and an inert gas can be separately fed to the fluidized-bed reactor 1 from different feed openings for the respective gases.

<Catalyst>

The ammoxidation catalyst for use in the present invention is of high activity, which can attain a rate constant of at least 2 s$^{-1}$, preferably 3 s$^{-1}$ or more, more preferably 4 s$^{-1}$ or more for the ammoxidation reaction of propylene, assuming that the reaction is a first-order reaction. As such a highly-active ammoxidation catalyst, any conventionally-known one can be used as long as it does not contravene the object of the invention. Typical examples of highly-active ammoxidation catalysts that can be preferably used in the present Invention include those ones which comprise as essential components iron, antimony and molybdenum. Examples of these catalysts include those described in Japanese Patent Publications No. 18014/1978 and No. 26592/1982, Japanese Patent Laid-Open Publication No. 118051/1992, and the like. As those catalysts which can reveal the inherent properties of highly-active catalysts, thereby particularly improving the effect of the present invention of attaining high yield and high productivity in the production of acrylonitrile, catalysts containing iron, antimony and molybdenum and, in addition to these elements, two elements selected from the group consisting of potassium, rubidium, cesium, manganese, cobalt, nickel, copper, zinc, boron, tin, tellurium, bismuth and cerium, specifically those catalysts which are represented by the following general formula can be preferably used:

$$Fe_aSb_bMo_cQ_dR_eS_fO_g$$

wherein Q represents at least one element selected from the group consisting of K, Rb and Cs; R represents at least one element selected from the group consisting of Mn, Co, Ni, Cu and Zn; S represents at least one element selected from the group consisting of B, P, Te, Bi and Ce; and the indexes a, b, c, d, e, f and g represent an atomic ratio, where when a is 10, b, c, d, e and f are $5 \leq b \leq 60$, $5 \leq c \leq 30$, $0 \leq d \leq 5$, $0.1 \leq e \leq 10$ and $0.01 \leq f \leq 5$, and g represents the number of oxygens corresponding to an oxide produced when the above components are combined.

The catalyst for use in the present invention is as follows: the range of particle diameters is generally from 5 to 300 μm, preferably from 10 to 200 μm (the "range of particle diameters" as used herein is a range of particle diameters corresponding to the weight-based cumulative values between 0.1% and 99.9% in a weight-based cumulative distribution determined by sieve analysis); an average particle diameter is generally from 30 to 80 μm, preferably from 40 to 65 μm (the "average particle diameter" as used herein is a particle diameter corresponding to the weight-based cumulative value of 50% in a weight-based cumulative distribution determined by sieve analysis); and a bulk density is generally from 0.6 to 1.5 g/cm³, preferably from 0.7 to 1.3 g/cm³ (the "bulk density" as used herein is a density determined by measuring the mass of a catalyst which has been packed in a measuring cylinder without shaking the cylinder, and converting it into a mass per unit volume).

Further, the highly-active ammoxidation catalyst according to the present invention is used as a high-velocity fluidized bed, so that it should be tough. In the present invention, preferable catalysts are such that 90% or more, preferably 95% or more of 20–75 μm particles have a compressive strength (CS) which can fulfill the following inequality:

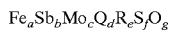

$$CS > A \cdot d^\alpha$$

wherein CS represents a compressive strength (g-weight/particle], A represents the constant of 0.001, d represents a particle diameter [μm], and α represents the constant of 2. In recent years, apparatuses by which the compressive strength of particles having such small diameters can be measured are on the market. Some proper apparatuses are currently available. However, the compressive strength (CS) as defined in the present invention is a value measured by using a "Shimadzu MCTM-200" manufactured by Shimadzu Corp., Japan under the following conditions:

Indenter:
 upper pressure indenter: diamond-made indenter having a face of 500 μm
 lower pressure plate: SUS plate
 Loading rate: 0.72 g-weight/sec Further, the 20–75 μm particles mean that the diameters of particles are, or an average of the lengths and breadths of particles is in the range of 20 to 75 μm. Specifically, such particles can be obtained by means of sieving using micromesh high-precision sieves manufactured by Buckbee Mears. Co., St. Paul. It is noted that samples are randomly taken from the 20–75 μm particles and that the number of the samples taken is statistically significant one.

In the case where more than 10% of 20–75 μm particles do not fulfill the above-described inequality relating to compressive strength (CS), the catalyst loss is great. Such a catalyst is therefore unsuitable for practical use. There is such a tendency that the larger the proportion of particles which do not fulfill the above inequality, the greater the catalyst loss.

<Production of Acrylonitrile>

The reaction temperature at which acrylonitrile is produced is generally from 400 to 500° C., preferably from 420 to 470° C. The reaction pressure is generally from atmospheric pressure to 5 kg/cm² gage, preferably from atmospheric pressure to 2 kg/cm² gage.

The materials to be fed to the reactor are such that the molar ratio of oxygen/propylene is generally from 1.5 to 3.0, preferably from 1.8 to 2.5 and that the molar ratio of ammonia/propylene is generally from 0.8 to 2.0, preferably from 1.0 to 1.5. The feed gas-ammoxidation catalyst contact time is generally from 0.1 to 20 seconds, preferably from 1 to 10 seconds.

EXAMPLES

The constant and the property values used in the following examples are determined as follows.

Rate constant of reaction $[1/s]=\mathrm{Ln}\{100/(100-\text{conversion of propylene }[\%])\}/(\text{contact time }[s])$ Contact time $[s]=(\text{weight of catalyst existing above propylene-feed opening }[kg])/\{(\text{bulk density of catalyst }[kg/m^3])\times(\text{volumetric flow rate of whole feed gas under reaction conditions }[m^3/s])\}$ Conversion of propylene $[\%]=\{(\text{weight of carbon contained in propylene reacted }[kg])/(\text{weight of carbon contained in propylene fed }[kg])\}\times 100$ Yield of acrylonitrile $[\%]=\{(\text{weight of carbon contained in acrylonitrile produced }[kg])/(\text{weight of carbon contained in propylene fed }[kg])\}\times 100$ Example 1

Acrylonitrile was produced by the ammoxidation of propylene using a reactor as shown in FIG. 1. Specifically, to the bottom of a fluidized-bed reactor as shown in FIG. 1, having an inner diameter of 0.04 m and a height of 10 m, a feed gas consisting of 8.5 mol % of propylene, 10.3 mol % of ammonia, and air as the remainder was fed; and the superficial gas velocity in the reactor was maintained at 4 m/sec under such conditions that the reaction temperature was 435° C. and that the pressure at the top of the reactor was 0.80 kg/cm²G. The ammoxidation catalyst used was a highly-active ammoxidation catalyst (the rate constant of the reaction was 7.7 s⁻¹ under the operation conditions) supported on silica, represented by the following empirical formula:

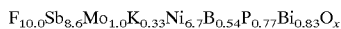
$F_{10.0}Sb_{8.6}Mo_{1.0}K_{0.33}Ni_{6.7}B_{0.54}P_{0.77}Bi_{0.83}O_x$ wherein x represents an atomic ratio of oxygen when the above components are combined, having particle diameters ranging from 5 to 300 μm, an average particle diameter of approximately 50 μm, and a bulk density of 1.0 g/cm³.

The separation of the catalyst from the reaction product gas was performed in a cyclone provided at the outlet of the reactor. The catalyst separated was introduced into the reactor through a catalyst feed opening at such a position that the weight ratio of the ammoxidation catalyst present in an area above the position to the ammoxidation catalyst present in an area below the position was 19:1. At this time, an area in which the density of the catalyst solid was 200 kg/m³ was formed between the bottom of the reactor and the opening through which the catalyst was returned to the reactor for recycling.

The yield of acrylonitrile was determined by the gas-chromatographic analysis of a solution obtained by allowing an aqueous hydrochloric acid solution to absorb the reaction product gas; and the conversion of propylene was determined by measuring, by gas-chromatographic analysis, unreacted propylene contained in the unabsorbed gas. As a result of the reaction and measurement, the conversion of propylene was 99%, and the yield of acrylonitrile was 82.5%.

It may be appreciated from these results that, according to the present invention, propylene can be ammoxidized into acrylonitrile at high conversion and in high yield in a fluidized-bed reactor using a highly-active catalyst.

Example 2

The procedure of Example 1 was repeated except that a fluidized-bed reactor shown in FIG. 2, a feed gas consisting of 8.6 mol % of propylene, 10.5 mol % of ammonia and air as the remainder, and a catalyst represented by the following empirical formula:

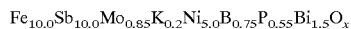
$Fe_{10.0}Sb_{10.0}Mo_{0.85}K_{0.2}Ni_{5.0}B_{0.75}P_{0.55}Bi_{1.5}O_x$ were used instead of those used in Example 1. The catalyst used had the following features: the catalytic activity was such that the rate constant of the reaction became 7.8 s⁻¹ under the operation conditions; the range of particle diameters was from 5 to 300 μm; the average particle diameter was 55 μm; and the bulk density was 1.0 g/cm³.

The position at which the catalyst separated was introduced from the recycling system into the reactor was such that the weight ratio of the ammoxidation catalyst present in an area above the position to the ammoxidation catalyst present in an area below the position was 19:1. In this example, an area in which the density of the catalyst solid was 250 kg/cm³ was kept between the bottom of the reactor and the opening for introducing the catalyst.

The reaction conditions and the results are as shown in Table 1. It can be seen from these results that, according to the present invention, propylene can be ammoxidized into acrylonitrile at high conversion and in high yield in a fluidized-bed reactor using a highly-active catalyst.

Example 3

The procedure of Example 2 was repeated except that only air was fed to the bottom of the fluidized-bed reactor and that propylene and ammonia were fed to the reactor at such a position that the weight ratio of the ammoxidation catalyst present in an area above the feed position to the ammoxidation catalyst present in an area below the position was 8:2. The reaction conditions and the results are as shown in Table 1.

Since the position of the feeding of propylene and ammonia was shifted from the bottom of the fluidized-bed reactor to the upper part of the same, the contact time of the ammoxidation catalyst and the feed gas was decreased. However, a decrease in the conversion was significantly smaller than that expected from the decrease in the contact time. This indicates that it is possible to maintain the rate constant of the reaction and the yield of acrylonitrile high by activating the catalyst by introducing air into the regeneration area.

Comparative Example 1

Reaction was carried out under the same conditions as in Example 1 except that a fluidized-bed reactor having an inner diameter of 0.04 m and a height of 1 m was used and that the superficial gas velocity in the reactor and the contact time were changed to 0.1 m/s and 1.75 seconds, respectively. The reaction conditions and the results are as shown in Table 1. It is apparent from the results that the yield in Example 1 in which a recycling fluidized-bed reactor was used is considerably higher than the yield in this Comparative Example 1 in which a conventional fluidized-bed reactor was used.

TABLE 1

| Example No. | Reaction area | | | | | Results of reaction | |
| --- | --- | --- | --- | --- | --- | --- | --- |
| | Temperature | Contact time | Feed gas (mol %) | | | Conversion (%) | Yield of acrylonitrile (%) |
| | | | Propylene | Ammonia | Air | | |
| Ex. 1 | 435° C. | 0.60 sec | 8.5 | 10.3 | 81.2 | 99.0 | 82.5 |
| Ex. 2 | 435° C. | 0.60 sec | 8.6 | 10.5 | 80.9 | 99.1 | 82.3 |
| Ex. 3 | 435° C. | 0.55 sec | 8.6 | 10.5 | 80.9 | 98.9 | 82.3 |
| Comp. Ex. 1 | 435° C. | 1.75 sec | 8.5 | 10.3 | 81.2 | 98.1 | 80.4 |

What is claimed is:

1. In a process for producing acrylonitrile by the ammoxidation of propylene, comprising bringing, in a fluidized-bed reactor, a gas containing propylene, ammonia and molecular oxygen into contact with a highly active ammoxidation catalyst, this catalyst being one which may attain a rate constant of reaction of 2 s$^{-1}$ or more for the ammoxidation reaction of propylene, which is in a state of being fluidized by the gas, the improvement comprising carrying out the ammoxidation under the following conditions:

(a) the superficial gas velocity in the fluidized-bed reactor is maintained at 1 to 10 m/s under such an operation condition that the rate constant of the ammoxidation reaction of propylene is 2 s$^{-1}$ or more;

(b) an area in which the density of fluidized solid matter is 100 kg/m$^3$ or more is kept in the fluidized-bed reactor at the upstream side thereof; and (c) a system for recycling the ammoxidation catalyst which has been supplied to the reaction is provided in the fluidized-bed reactor between the upstream side and downstream side thereof, and the recycling catalyst is introduced into the reactor at such a position that the weight ratio of the ammoxidation catalyst present in an area above the introduction position to the ammoxidation catalyst present in an area below the position will be from 2:1 to 99:1, and wherein the constant of reaction (1/s)=Ln{100/(100−conversion of propylene (%))}/(contact time (s))

contact time (s),=(weight of catalyst existing above propylene-feed opening (kg))/{(bulk density of catalyst (kg/m$^3$))×(volumetric flow rate of whole feed gas under reaction conditions (m$^3$/s))}, and the conversion of propylene (%)={(weight of carbon contained in propylene reacted (kg))/(weight of carbon contained in propylene fed (kg))}×100, and wherein the highly-active ammoxidation catalyst has a composition represented by the following general formula:

$$Fe_aSb_bMo_cQ_dR_eS_fO_g$$

wherein Q represents at least one element selected from die group consisting of K, Rb and Cs; R represents at least one element selected from the group consisting of Mn, Co, Ni, Cu and Zn; S represents at least one element selected from the group consisting of B, P, Te, Bi and Ce; and the indexes a, b, c, d, e, f and g represent an atomic ratio, where, when a is 10, b, c, d, c and f are 5≦b≦60, 5≦c≦30, 0≦d≦5, 0.1≦e≦10 and 0.01≦f≦5, and g represents the number of oxygens corresponding to an oxide produced when the above components are combined.

2. The process according to claim 1, wherein the recycling catalyst is introduced into the fluidized-bed reactor after it is subjected to a reactivation treatment which comprises bringing the catalyst into contact with a molecular oxygen-containing gas.

3. The process according to claim 1, wherein the highly-active ammoxidation catalyst has particle diameters ranging from 5 to 300 μm, an average particle diameter of approximately 30 to 80 μm, and a bulk density of approximately 0.6 to 1.5 g/cm$^3$.

4. The process according to claim 2, wherein the reactivation treatment is carried out at a temperature of 450 to 700° C.

5. The process according to claim 1, wherein the ammoxidation is carried out at a temperature of 400 to 500° C.

* * * * *